United States Patent [19]

Aoki et al.

[11] 4,332,886
[45] Jun. 1, 1982

[54] COLOR PHOTOGRAPHIC LIGHT-SENSITIVE MATERIAL INCLUDING AN ORGANIC SPIROBIS COMPOUND COLOR COUPLER

[75] Inventors: Kozo Aoki; Tetsuro Kojima; Nobuo Furutachi; Satoru Sawada, all of Minami-ashigara, Japan

[73] Assignee: Fuji Photo Film Co., Ltd., Kanagawa, Japan

[21] Appl. No.: 195,166

[22] Filed: Oct. 8, 1980

[30] Foreign Application Priority Data

Oct. 8, 1979 [JP] Japan .................... 54-129773

[51] Int. Cl.$^3$ .................................. G03C 1/10
[52] U.S. Cl. ........................... 430/551; 430/372; 430/233
[58] Field of Search .................. 430/551, 372, 233

[56] References Cited

U.S. PATENT DOCUMENTS 4,279,990 7/1981 Aoki et al. ................ 430/551

Primary Examiner—John D. Welsh
Attorney, Agent, or Firm—Sughrue, Mion, Zinn, Macpeak and Seas

[57] ABSTRACT

A color photographic light-sensitive material containing, in a photographic layer, a coupler and at least one compound represented by the formula (I), or at least one bis-compound (inclusive spirobis-compound) thereof,

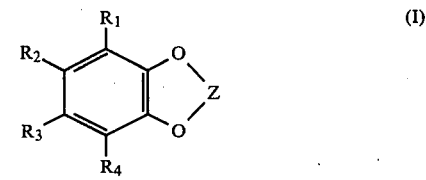

wherein Z represents an alkylene group having from 1 to 3 carbon atoms which can be substituted with one or more of hydrogen, a halogen atom, an alkyl group, an aryl group, an alkoxy group, an aryloxy group, a=S group or a=O group; and $R_1$, $R_2$, $R_3$, and $R_4$ each represents hydrogen, a halogen atom, an alkyl group, an aryl group, an alkoxy group, an aryloxy group, an alkylthio group, an acyl group, an acylamino group, a sulfonamido group, a diacylamino group, a carboxy group, a sulfo group, or a hydroxy group, or $R_1$ and $R_2$ and $R_3$ together form a group represented by

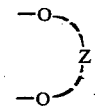

(wherein Z has the same meaning as Z in formula (I)) or a 5-membered or 6-membered hydrocarbon ring or hetero-cyclic ring is described.

The compounds represented by formula (I) are effective in preventing the fading of dye images formed upon color development of the color photographic light-sensitive material and the occurrence of yellow stain in non-image areas due to the action of light, humidity or heat.

28 Claims, No Drawings

COLOR PHOTOGRAPHIC LIGHT-SENSITIVE MATERIAL INCLUDING AN ORGANIC SPIROBIS COMPOUND COLOR COUPLER

BACKGROUND OF THE INVENTION

1. Field of the Invention

The present invention relates to a color photographic light-sensitive material and, more particularly, it relates to preventing the fading of dye images obtained upon development-processing a color photographic light-sensitive material, and preventing discoloration (e.g., yellowing) of uncolored areas (hereinafter referred to as white background).

2. Description of the Prior Art

Color images obtained by photographically processing a silver halide color photographic light-sensitive material comprise, in general, an azomethine dye or indoaniline dye image formed by the reaction between an oxidation product of an aromatic primary amine developing agent and a coupler.

The thus-obtained color photographic images typically are stored for long periods of time as records, or are displayed. However, known photographic images are not completely stable to light, humidity or heat. When exposed to light for a long period of time or stored under high temperature and humidity conditions, the dye images tend to fade or discolor and, in addition, the white background is colored, usually resulting in a deterioration of image quality.

This fading and discoloration of images are quite serious defects in a recording material. The following compounds have heretofore been used to remove these defects. For example, hydroquinone derivatives including 2,5-tert-butylhydroquinone, phenol derivatives such as 2,6-di-tert-butyl-p-cresol, 4,4'-methylenebis(2,6-di-tert-butylphenol), 2,2'-methylenebis(4-ethyl-6-tert-butylphenol), 4,4'-isopropylidenediphenol, etc., and tocopherols are representative of such compounds.

Furthermore, the compounds in which the hydroxy group of the hydroquinone derivatives, the phenol derivatives or the chroman derivatives such as tocopherols is substituted with an alkoxy group or an acyloxy have recently been described in Japanese Patent Application (OPI) No. 17729/53 and West German Patent Application (OLS) No. 2,735,206.

These compounds are effective to some extent as an agent for preventing fading or discoloration of dye images. However, the effect is not completely satisfactory or, although some compounds may prevent fading, they deteriorate hue, generate fog, lower dispersion property or form crystals. Thus, no satisfactory color image stabilizers which exhibit completely excellent effects for photographic use are known.

SUMMARY OF THE INVENTION

An object of the present invention is to provide a color photographic light-sensitive material capable of providing stable color images which comprises a color photographic light-sensitive material containing in a photographic layer a color image stabilizer having an effect sufficient to prevent fading or discoloration of color images without the deterioration of hue and the generation of fog.

Another object of the present invention is to provide a color photographic light-sensitive material capable of preventing the formation of yellow stain in unexposed areas of the photographic material after development processing due to effects of light, heat or humidity.

As a result of extensive investigations, it has now been discovered that the objects of the present invention can be attained by the incorporation, in a photographic layer of a color photographic light-sensitive material, of at least one compound represented by the formula (I), or at least one bis-compound (inclusive spirobis-compound) thereof,

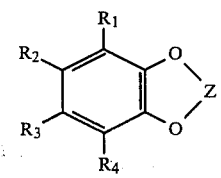

(I)

where Z represents an alkylene group having from 1 to 3 carbon atoms which can be substituted with one or more of hydrogen, a halogen atom, an alkyl group, an aryl group, an alkoxy group, an aryloxy group, a $=S$ group, or a $=O$ group (wherein the substituents may be the same or different); and $R_1$, $R_2$, $R_3$ and $R_4$ each represents hydrogen, a halogen atom, an alkyl group, an aryl group, an alkoxy group, an aryloxy group, an alkylthio group, an acyl group, an acylamino group, a sulfonamido group, a diacylamino group, a carboxy group, a sulfo group or a hydroxy group, or, $R_1$ and $R_2$ or $R_2$ and $R_3$ together form a group represented by

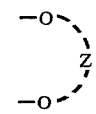

(wherein Z has the same meaning as Z in formula (I)) or a 5-membered or 6-membered hydrocarbon ring or hetero-cyclic ring.

DETAILED DESCRIPTION OF THE INVENTION

Useful substituents for Z in the formula (I) are described in more detail below. Such substituents for Z are selected from the members consisting of hydrogen, a halogen atom, a straight chain, branched-chain, or cyclic alkyl group having from 1 to 32 carbon atoms (for example, a methyl group, an ethyl group, an isopropyl group, a tert-butyl group, an n-octyl group, a tert-octyl group, a dodecyl group, a cyclohexyl group, a hexadecyl group, a benzyl group, etc.), an aryl group having from 6 to 32 carbon atoms (for example, a phenyl group, an 1-naphthyl group, etc.), an alkoxy group having from 1 to 32 carbon atoms (for example, a methoxy group, an ethoxy group, an n-octyloxy group, a tert-octyloxy group, a 2-ethylhexyloxy group, a dodecyloxy group, a hexadecyloxy group, an octadecyloxy group, a benzyloxy group, etc.), and an aryloxy group having from 6 to 32 carbon atoms (for example, a phenoxy group, an 1-naphthoxy group, etc.). The alkyl group, the aryl group, the alkoxy group and the aryloxy group may be substituted with one or more of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

$R_1$, $R_2$, $R_3$ and $R_4$ in formula (I) are described in more detail below. $R_1$, $R_2$, $R_3$ and $R_4$ each can represent hydrogen, a halogen atom, a straight chain, branched chain or cyclic alkyl group having 1 to 32 carbon atoms (for example, a methyl group, an ethyl group, an isopropyl group, a tert-butyl group, an n-octyl group, a tert-octyl group, a dodecyl group, a tert-amyl group, a 1,1-dimethylbutyl group, a cyclohexyl group, a hexadecyl group, a cyclohexyl group, a benzyl group, etc.), an aryl group having from 6 to 32 carbon atoms (for example, a phenyl group, an 1-naphthyl group, etc.), an alkoxy group having from 1 to 32 carbon atoms (for example, a methoxy group, an ethoxy group, an n-octyloxy group, a tert-octyloxy group, a 2-ethylhexyloxy group, a dodecyloxy group, a hexadecyloxy group, an octadecyloxy group, a benzyloxy group, etc.), an aryloxy group having from 6 to 32 carbon atoms (for example, a phenoxy group, an 1-naphthoxy group, etc.), an alkylthio group having from 1 to 32 carbon atoms (for example, a methylthio group, an n-octylthio group, an n-dodecylthio group, an n-octadecylthio group, etc.), an acyl group having from 1 to 32 carbon atoms (for example, an acetyl group, an octanoyl group, a tetradecanoyl group, a benzoyl group, etc.), an acylamino group having from 1 to 32 carbon atoms (for example, an acetamido group, a tetradocanamido group, a benzamido group, etc.), a sulfonamido group having from 1 to 32 carbon atoms (for example, a methanesulfonamido group, an ethanesulfonamido group, a benzenesulfonamido group, etc.) or a diacylamino group having from 2 to 32 carbon atoms (for example, an 1-succinimido group, an 1-phthalimido group, an 1-hydantoinyl group, a 2,4-dioxo-3-oxazinyl group, etc.). The alkyl group, the aryl group, the alkoxy group, the aryloxy group, the alkylthio group, the acyl group, the acylamino group, the sulfonamido group and the diacylamino group may be substituted with one or more of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, an diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

Further, $R_1$, $R_2$, $R_3$ and $R_4$ can each represent a carboxy group, a sulfo group, or a hydroxy group.

Furthermore, the hydrocarbon ring which is formed by bonding $R_1$ and $R_2$ or $R_2$ and $R_3$, together with the benzen ring to which they are attached, includes, for example, an indan ring, a naphthalene ring, a tetrahydronaphthalene ring, etc., and further the indan rings may form a spiroindan ring. The hydrocarbon ring may be substituted with one or more of a halogen atom, a nitro group, a cyano group, a thiocyano group, an alkyl group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, hydroxy group or a mercapto group.

Also, the spiroindan ring includes a spiroindan ring substituted with

groups (wherein Z has the same meaning as Z in formula (I)) which can be represented by the formula (II)

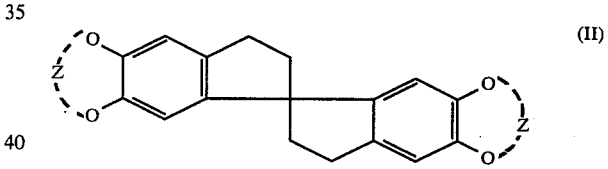

(II)

Moreover, the hetelocyclic ring which $R_1$ and $R_2$ or $R_2$ and $R_3$, together with the benzen ring to which they are attached, includes, for example, a chroman ring, a coumaran ring, etc., and further the chroman rings or the coumaran rings may form a spirochroman ring or a spirocoumaran ring respectively. The heterocyclic ring may be substituted with one or more of a halogen atom, a nitro group, a cyano group, a thiocyano group, an alkyl group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, ureido group, a thioureido group, urethane group, thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

Also, the spirochroman ring or the spirocoumaran ring includes a spirochroman ring or a spirocoumaran ring which is substituted with

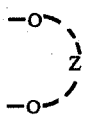

group (wherein Z has the same meaning as Z in formula (I)) can represent the formula (III) or the formula (IV)

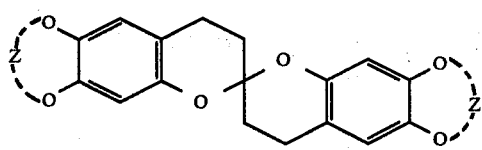

(III)

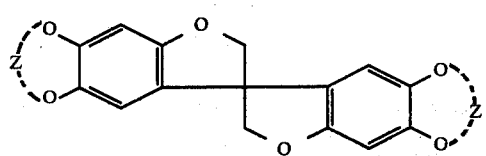

(IV)

Of the compounds represented by formula (I), those compounds in which Z represents an unsubstituted alkylene group or an alkylene group substituted with an alkyl group or an aryl group are preferred. For $R_1$, $R_2$, $R_3$ and $R_4$, hydrogen, a halogen atom, an alkyl group, an alkoxy group and an alkylthio group are preferred. Of the rings formed on the positions of $R_1$ and $R_2$ and $R_2$ and $R_3$, a ring formed on the position of $R_2$ and $R_3$ is preferred. The compounds in which $R_2$ and $R_3$ together form a group represented by

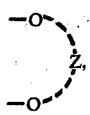

(wherein Z has the same meaning as Z in formula (I)), are also preferred. Of the compounds in which $R_2$ and $R_3$ are bonded each other, a chroman ring and a spirochroman ring are preferred.

Furthermore, particularly preferred effects are obtained when the compound represented by formula (I) is employed together with a magenta coupler, particularly a 5-pyrazolone type compound, or a cyan coupler, particularly a phenol or naphthol derivative.

Moreover, more superior effects are achieved when the compound represented by the formula (I) is used in a combination with a known fade-preventing agent such as a hydroquinone compound, a hydroxychroman compound, a hydroxyspirochroman compound, a compound wherein the hydroxy group of a hydroxychroman or hydroxyspirochroman compound is substituted with an alkoxy group, or an alkoxyphenol compound.

The color image stabilizer of formula (I) used in the present invention is suitably employed, e.g., in an amount of from about 0.5 to 200% by weight, and preferably from 2 to 150% by weight, based on the weight of coupler, although the amount thereof will vary some depending upon the particular type of coupler or couplers employed.

Typical examples of these compounds are illustrated below, but the compounds which can be used in the present invention are not to be construed as being limited to these examples.

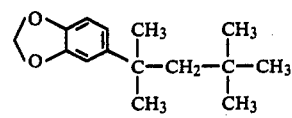

(1)

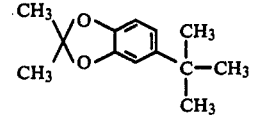

(2)

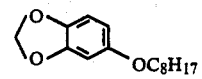

(3)

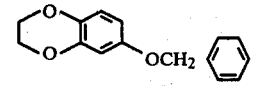

(4)

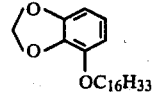

(5)

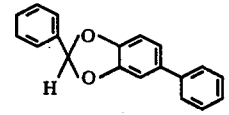

(6)

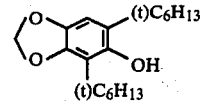

(7)

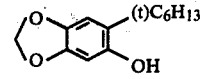

(8)

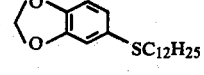

(9)

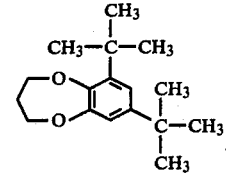

(10)

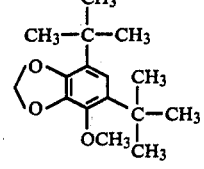

(11)

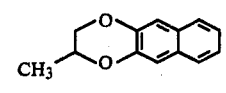

(12)

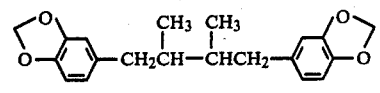

(13)

-continued

(14) 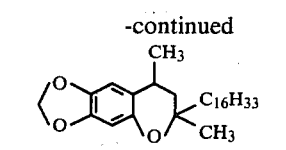

(15) 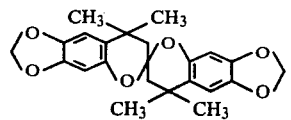

(16) 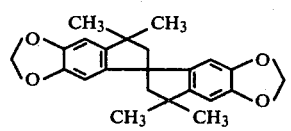

(17) 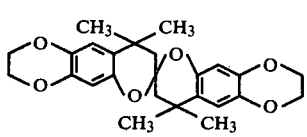

(18) 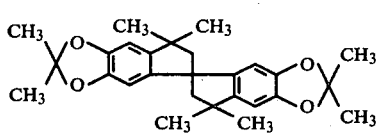

(19) 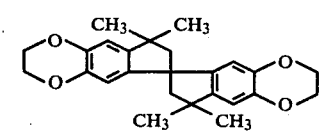

(20) 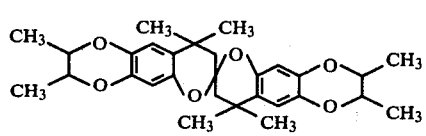

(21) 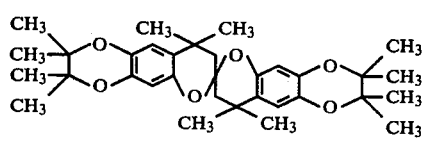

(22) 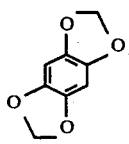

(23) 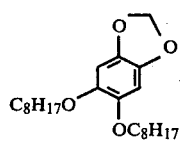

(24) 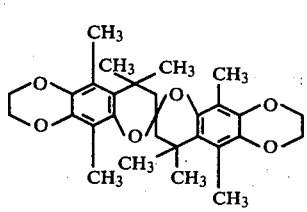

-continued

(25) 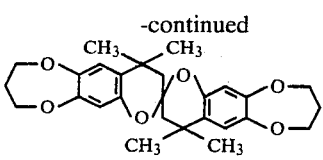

(26) 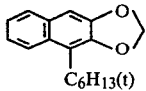

(27) 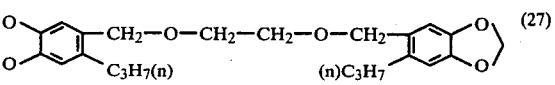

(28) 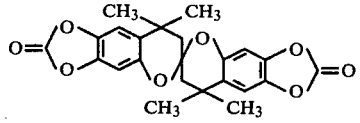

The compounds according to the present invention can be synthesized, in general, by one or both of the following two synthesis methods (1) Reaction of a corresponding catechol with an alkylene dihalide in the presence of a base.

(2) Acetal exchange reaction between a corresponding catechol and an acetal of aldehyde in the presence of an acid catalyst.

Specific synthesis examples of the compounds are illustrated below. Other compounds can be synthesized in a similar manner.

SYNTHESIS EXAMPLE 1

Synthesis of 4,4,4',4'-tetramethyl-6,7,6',7'-bismethylenedioxy-2,2'-spirobischroman [Compound (15)]

15 g (0.04 mol) of 6,7,6',7'-tetrahydroxy-4,4,4',4'-tetramethyl-2,2'-spirobischroman was dissolved in 100 m of benzene, and to the solution 28 g (0.08 mol) of methylene bromide and 2.5 g (0.008 mol) of tetrabutylammonium bromide were added. To the mixture a solution containing 20 g (0.12 mol) of sodium hydroxide dissolved in 50 ml of water was added, and the mixture was vigorously stirred for 8 hours while refluxing by heating. After cooling, the mixture was washed with water and the organic layer was dried with anhydrous sodium sulfate. The solvent was removed under reduced pressure to obtain a crystalline residue. Upon recrystallization of the residue from acetonitrile, white crystals having the melting point of 197° to 199° C. were obtained (yield: 12 g, 74.5%).

Elemental Analysis: Calculated: C: 69.68%; H: 6.10%; Found: C: 69.43%; H: 6.14%.

SYNTHESIS EXAMPLE 2

Synthesis of 4,4,4',4'-tetramethyl-6,7,6',7'-bisethylenedioxy-2,2'-spirobischroman [Compound (17)]

15 g (0.04 mol) of 6,7,6',7'-tetrahydroxy-4,4,4',4'-tetramethyl-2,2'-spirobischroman was dissolved in 50 ml of dimethylformamide and to the solution 14 g (0.10 mol) of potassium carbonate was added followed by heating to 90° C. To the mixture 19 g (0.10 mol) of 1,2-dibromoethane was added dropwise and the mixture was stirred at 90° C. for 5 hours. The reaction mixture was poured into 1 liter of water and extracted with 1 liter of ethyl acetate. The organic layer was dried with anhydrous sodium sulfate. The solvent was removed under reduced pressure to obtain crystalline residue. Upon recrystallization of the residue from benzene, white crystals having the melting point of 303° to 304° C. were obtained (yield: 11 g, 64.8%).

Elemental analysis: Calculated: C: 70.74%; H: 6.65%; Found: C: 70.82%; H: 6.58%.

SYNTHESIS EXAMPLE 3

Synthesis of 3,3,3',3'-tetramethyl-5,6,5',6'-bisethylenedioxy-1,1'-spirobisindan [Compound (19)]:

24 g (0.07 mol) of 5,6,5',6'-tetrahydroxy-3,3,3',3'-tetramethyl-1,1'-spirobisindan was dissolved in 200 ml of benzene, and to the solution 26 g (0.14 mol) of 1,2-dibromoethane and 5 g (0.016 mol) of tetrabutylammonium bromide were added. To the mixture a solution containing 50 g (0.30 mol) of sodium hydroxide dissolved in 100 ml of water was added and the mixture was vigorously stirred for 5 hours while refluxing by heating. After cooling, the organic layer was washed with water and dried with anhydrous sodium sulfate. The solvent removed under reduced pressure to obtain a crystalline residue. Upon recrystallization of the residue from benzene, white crystals having a melting point of 267° to 268° C. were obtained (yield: 20 g, 72.8%).

Elemental Analysis Calculated: C: 76.50% M: 7.19% Found: C: 76.31% M: 7.35%

The photographic emulsion layer of the photographic light-sensitive material produced according to the present invention can contain a dye-image-forming coupler (also referred to herein more simply as a "coupler"), that is, a compound capable of forming a dye upon the reaction of the oxidation product of an aromatic amine (conventionally primary amine) developing agent therewith (hereinafter referred to as a coupler).

Non-diffusible couplers which contain a hydrophobic group, called a ballast group, in the molecule thereof are preferred as couplers. Couplers can be 4-equivalent or 2-equivalent couplers. In addition, colored couplers (couplers having a color per se) providing a color correction effect, or couplers which release development inhibitors upon development (so-called DIR couplers) can also be present therein. Also, couplers which provide a colorless product on coupling can be employed.

Conventional open chain ketomethylene type couplers can be employed as yellow-color-forming couplers. Of these couplers, benzoyl acetanilide type and pivaloyl acetanilide type compounds are especially effective. Specific examples of yellow-color-forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77 (the term "OPI" as used herein referred to a "published unexamined Japanese patent application").

Pyrazolone type compounds, indazolone type compounds cyanoacetyl compounds, etc., can be employed as magenta color forming couplers, and particularly preferred couplers are pyrazolone type compounds. Specific examples of magenta-color-forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, etc.

Phenol type compounds, naphthol type compounds, etc., can be employed as cyan-color-forming couplers. Specific examples of cyan-color-forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329, Japanese Patent Application (OPI) Nos. 59838/73, 26034/76, 5055/73, 146828/76, 69624/77 and 90932/77, etc.

Colored couplers which can be employed include those described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, German Patent Application (OLS) No. 2,418,959, etc.

DIR couplers which can be employed include those described, for example, in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77, 122335/74, Japanese Patent Publication No. 16141/76, etc.

In addition to DIR couplers, other compounds which release development inhibitors upon development can also be present in the light-sensitive material. For example, such DIR compounds as are described in U.S. Pat. Nos. 3,297,445 and 3,379,529, German Patent Application (OLS) No. 2,417,914, Japanese Patent Application (OPI) Nos. 15271/77 and 9116/78, etc. can be employed.

Two or more kinds of the couplers described above can be incorporated in the same layer, or the same coupler compound can also be present in two or more layers.

These couplers are incorporated into the emulsion layers, generally in an amount of from about $2 \times 10^{-3}$ mol to $5 \times 10^{-1}$ mol, and preferably from $1 \times 10^{-2}$ mol to $5 \times 10^{-1}$ mol, per mol of silver (present in the form of silver halide).

In practicing the present invention, known antifading agents can be used together with the compound according to the present invention, and the color image stabilizer of the present invention can be used individually or as combinations of two or more. Specific known antifading agents include, for example, the hydroquinone derivatives described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921, etc., the gallic acid derivatives described in U.S. Pat. Nos. 3,457,079 and 3,069,262, etc., the p-alkoxyphenols described in U.S. Pat. Nos. 2,735,765 and 3,698,909, Japanese Patent Publication Nos. 20977/74 and 6623/77, etc., the p-oxyphenol derivatives described in U.S. Pat. Nos. 3,432,300, 3,573,050, 3,574,627 and 3,764,337, Japanese Patent Application (OPI) Nos. 35633/77, 14743/77 and 152225/77, the bisphenols described in U.S. Pat. No. 3,700,455, etc.

To incorporate the compound of the present invention (color image stabilizer) into a photographic layer of a color light-sensitive material, it is possible, for example, to dissolve the compound in a low boiling organic solvent such as ethyl acetate, ethanol, etc., and directly add the solution thereof to a silver halide emulsion or to a coupler dispersion mixture without emulsification. However, it is more desirable to dissolve the compound of the present invention (color image stabilizer) in a high boiling organic solvent such as dibutyl phthalate, tricresyl phosphate, etc., together with a coupler and, if desired, in the presence of a low boiling auxiliary solvent and add such to a silver halide emulsion as an emulsion dispersion of the color image stabilizer together with a coupler dispersed as oil droplets in a water-soluble protective colloid such as gelatin or as an emulsion dispersion of the color image stabilizer alone together with a coupler dispersion.

Illustrative photographic layers to which the compound of the present invention (color image stabilizer) can be added include coupler-containing silver halide light-sensitive emulsion layers (e.g., a red-sensitive silver halide emulsion layer, a green-sensitive silver halide emulsion layer, a blue-sensitive silver halide emulsion layer) and light-insensitive photographic auxiliary layers (e.g., a protective layer, a filter layer, an interlayer, a subbing layer, etc.), in the color photographic light-sensitive material.

In particular, it is preferred for the color image stabilizer of the present invention be present in a magenta coupler-containing photographic layer. That is, the compound is particularly effective for preventing fading or discoloration of magenta images.

Typical examples of high boiling organic solvents which can be used for dispersing the color image stabilizer of the present invention alone or in combination with a coupler include butyl phthalate, dinonyl phthalate, butyl benzoate, diethylhexyl sebacate, butyl stearate, dinonyl maleate, tributyl citrate, tricresyl phosphate, dioctyl butyl phosphate, trihexyl phosphate, trioctadecyl phosphate, etc. as described in U.S. Pat. No. 3,676,137, diethyl succinate, dioctyl adipate, 3-ethylbiphenyl, liquid dye stabilizers described, as improved photographic dye image stabilizers, in *Product Licensing Index*, Vol. 83, pp. 26–29 (March, 1971).

Examples of low boiling organic solvents which can be used as auxiliary solvents together with a high boiling organic solvent include ethyl acetate, butyl acetate, ethyl propionate, ethyl formate, butyl formate, nitroethane, carbon tetrachloride, chloroform, hexane, cyclohexane, ethylene glycol, acetone, ethanol, dimethylformamide, dioxane, etc. In addition, it is also possible to use benzene, toluene, xylene, etc., with these solvents.

Surface active agents can also be used in dispersing a solution of the color image stabilizer alone or in combination with a coupler in an aqueous protective colloid solution, and illustrative examples thereof include saponin, sodium alkylsulfosuccinates, sodium alkylbenzenesulfonates, etc., and examples of the hydrophilic protective colloid which can be used are gelatin, casein, carboxymethyl cellulose, polyvinyl alcohol, polyvinyl pyrrolidone, styrene-maleic anhydride copolymers, condensates of styrene-maleic anhydride copolymers and polyvinyl alcohol, polyacrylic acid salts, ethyl cellulose, etc. However, the present invention is not limited only to these examples.

Suitable supports which can be used in the present invention include those which are commonly used for photographic light-sensitive materials such as a cellulose nitrate film, a cellulose acetate film, a cellulose acetage butyrate film, a cellulose acetate propionate film, a polystyrene film, a polyethylene terephthalate film, a polycarbonate film, a laminate of these films, a thin glass plate, paper, and the like. Papers coated or laminated with baryta or an α-olefin polymer, in particular, a polymer of an α-olefin having 2 to 10 carbon atoms such as polyethylene, polypropylene, an ethylene-butene copolymer, etc., synthetic resin films whose surface has been roughened to improve intimately the adhesive property with other polymers as described in Japanese Patent Publication No. 19068/72 also provide good results.

Suitable supports include transparent or opaque supports which are selected depending upon the end-use of the light-sensitive materials. Also, transparent supports colored with a dye or pigment can be used.

Suitable opaque supports include intrinsically opaque supports, such as paper and, in addition, that prepared by adding dyes or pigments like titanium oxide to a transparent film, a synthetic resin film which has been surface-treated according to the method described in Japanese Patent Publication No. 19068/72 papers or synthetic resin films to which carbon black, a dye or the like has been added to render them completely light-intercepting, and the like. A subbing layer is usually provided on the support. The surface of the support may be subjected to a preliminary processing, such as a corona discharge, irradiation with ultraviolet light, flame treatment, etc.

In practicing the present invention, it is additionally effective and advantageous to prevent fading or discoloration by light by providing an ultraviolet light-absorbing layer on the upper surface of a photographic light-sensitive image-forming layer upon coating on a support.

The color processing agents such as color developing agents, bleaching agents, fixing agents, etc. used in the present invention are not limited and any conventional agent may be used. In particular, the present invention can advantageously be employed in silver-saving type color light-sensitive materials described in U.S. Pat. Nos. 3,902,905, etc. Also, the present invention is not limited by the kind of intensifying agents used for color intensifying processing as described in West German Patent Application (OLS) No. 181,390, Japanese Patent Application (OPI) No. 9728/73, Japanese Patent Publication 14625/77, etc.

The present invention is applicable to ordinary color light-sensitive materials, in particular, color light-sensitive materials for color prints. Further, it is applicable to the color photographic system described in U.S. Pat. Nos. 3,227,550, 3,227,551, 3,227,552, U.S. Provisional Patent Publication No. B 351,673, etc., in particular, to the color diffusion transfer photographic system.

Color photographic development processing is necessary after exposure in order to obtain dye images using the color photographic light-sensitive material of the present invention. Color photographic development processing fundamentally involves a color development step, a bleaching step, and a fixing step. In some cases, two of these steps are conducted in one processing. In addition, a combination of color development, first fixing and bleach-fixing is also possible. The development processing step is combined with, if necessary, a prehardening bath, a neutralizing bath, a first development (black-and-white development), an image-stabilizing bath, a washing or the like. A suitable processing temperature is in many cases about 18° C. or above. Particularly, the processing temperature can be about 20° C. to 60° C., and for more rapid processing is preferably from 30° C. to 60° C.

A suitable color developer solution which can be used is an alkaline aqueous solution having a pH of about 8 or higher, preferably 9 to 12, containing an aromatic primary amine type color developing agent. Preferred and typical examples of the above-described color developing agent are 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfoamidoethylaniline, 4-amino-N,N-dimethylaniline, 4-amino-3-methoxy-N,N-diethylaniline, 4-amino-3-methyl-N-ethyl-N-$\beta$-methoxyethylaniline, 4-amino-3-methoxy-N-ethyl-N-$\beta$-methoxyethylaniline, 4-amino-3-$\beta$-methanesulfoamidoethyl-N,N-diethylaniline, and the salts thereof (e.g., sulfates, hydrochlorides, sulfites, p-toluenesulfonates, etc.). Other examples are described in U.S. Pat. Nos. 2,193,015, 2,592,364, Japanese Patent Application (OPI) No. 64933/73, L.F.A. Mason, *Photographic Processing Chemistry*, pp. 226–229, Focal Press, London (1966), etc.

The color developer solution can further contain pH buffers such as alkali metal sulfites, carbonates, borates or phosphates, development inhibitors or anti-fogging agents such as bromides, iodides or organic anti-fogging agents.

Specific examples of the anti-fogging agents includes potassium bromide, potassium iodide, nitrobenzimidazoles, as described in U.S. Pat. Nos. 2,496,940 and 2,656,271, mercaptobenzimidazole, 5-methylbenzotriazole, 1-phenyl-5-mercaptotetrazole, compounds as described in U.S. Pat. Nos. 3,113,864, 3,342,596, 3,295,976, 3,615,522, 3,597,199, etc., thiosulfonyl compounds described in British Patent No. 972,211, phenazine-N-oxides, as described in Japanese Patent Publication No. 41675/71, anti-fogging agents as described in *Kagaku Shashin Binran*, Vol. 11, pp. 29–47, and the like.

In addition, the color developer solution may contain, if desired, a water softener, a preservative such as hydroxylamine, an organic solvent such as benzyl alcohol, diethylene glycol, etc., a development accelerator such as polyethylene glycol, a quaternary ammonium salt, an amine, etc., a dye-forming coupler, a competitive coupler, a fogging agent such as sodium borohydride, an auxiliary developing agent such as 1-phenyl-3-pyrazolidone, a viscosity-imparting agent, and the like.

The color light-sensitive material of the present invention can be subjected to ordinary color development processing or to the following color intensifying development processing: for example, a processing using peroxides described in U.S. Pat. Nos. 3,674,490, 3,761,265, West German Patent Application (OLS) No. 2056360, Japanese Patent Application (OPI) Nos. 6338/72, 10538/72, 13334/77, 13335/77 and 13336/77, etc.; a processing using cobalt complex salts described in West German Patent Application (OLS) No. 2,266,770, Japanese Patent Applications (OPI) Nos. 9728/73, 9729/73, 6026/76, 94822/76, 133023/76, 7728/77, 11034/77, etc.; and a processing using chlorous acid described in Japanese Patent Publication 14625/77, Japanese Patent Applications (OPI) Nos. 99022/76 and 103430/76, etc.

After color development processing, the photographic emulsion layer is usually subjected to bleaching. Bleaching may be conducted either simultaneously with fixing or independently thereof. Suitable bleaching agents which can be used include compounds of multivalent metals such as iron (III), cobalt (III), chromium (VI), copper (II), etc., peracids, quinones, nitroso compounds, etc. For example, ferricyanides, dichromates, organic complex salts of iron (III) or cobalt (III), complex salts of aminopolycarboxylic acids (e.g., ethylenediaminetetraacetic acid, nitrilotriacetic acid, 1,3-diamino-2-propanoltetraacetic acid, etc.) or of organic acids (e.g., citric acid, tartaric acid, malic acid, etc.); persulfates, permanganates; nitrosophenol, etc., can be used. Of these, potassium ferricyanide, iron (III) sodium ethylenediaminetetraacetate and iron (III) ammonium ethylenediaminetetraacetate are particularly useful. Ethylenediaminetetraacetic acid-iron (III) complex salt is effective in a bleaching solution and in a monobath bleach-fixing solution.

Various additives, including bleaching-accelerators as described in U.S. Pat. Nos. 3,042,520, 3,241,966, Japanese Patent Publication Nos. 8506/70, 8836/70, etc., can also be added to the bleaching solution or bleach-fixing solution.

The present invention is illustrated in greater detail by reference to the following examples which, however, are not to be construed as limiting the present invention.

EXAMPLE 1

10 g of 1-(2,4,6-trichlorophenyl)-3-[(2-chloro-5-tetradecanamido)anilino]-2-pyrazolin-5-one (a magenta coupler) was dissolved in a mixture of 20 ml of tricresyl phosphate and 20 ml of ethyl acetate, and the resulting solution was dispersed in 80 g of a aqueous gelatin solution containing 8 ml of a 1% aqueous solution of sodium dodecylbenzenesulfonate to obtain an emulsified dispersion. Then, this dispersion was mixed with 145 g of a green-sensitive silver chlorobromide emulsion (Bromide: 50 mol%) (containing 7 g of silver), sodium dodecylbenzenesulfonate was added as a coating aid and it was coated on a paper support both sides of which were laminated with polyethylene. The coated amount of the coupler was 400 mg/m$^2$. On this layer, a gelatin protective layer was coated (gelatin 1 g/m$^2$) to prepare Sample A.

In the same manner as for Sample A, except adding 3 g of each of the compounds according to the present invention and the comparative compounds as shown in Table I below when the dispersion was prepared, Sample B to L were prepared.

After exposing these samples for 1 second to light of 1,000 lux, they were processed in the following processing solutions.

| Color Developer Solution | |
|---|---|
| Benzyl Alcohol | 15 ml |
| Diethylenetriamine Pentaacetic Acid | 5 g |
| Potassium Bromide | 0.4 g |
| Sodium Sulfite | 5 g |
| Sodium Carbonate | 30 g |
| Hydroxylamine Sulfate | 2 g |

-continued

| | | |
|---|---|---|
| 4-Amino-3-methyl-N-ethyl-N-β-(methanesulfonamido)ethylaniline 3/2 sulfate Monohydrate | 4.5 g | |
| Water to make | 1000 ml (pH 10.1) | |
| Bleach-Fixing Solution | | |
| Ammonium Thiosulfate (70% aqueous solution) | 150 ml | |
| Sodium Sulfite | 5 g | |
| Sodium Ferric Ethylenediamine-tetraacetate | 40 g | |
| Ethylenediaminetetraacetic Acid | 4 g | |
| Water to make | 1000 ml (pH 6.8) | |

| Processing Step | Temperature | Time |
|---|---|---|
| Color Development | 33° C. | 3.5 min |
| Bleach-Fixing | 33° C. | 1.5 min |
| Washing | 28 to 35° C. | 3.0 min |

Each of these samples in which dye images had been formed was subjected to a fading test for 5 days using a Xenon tester (200,000 lux) equipped with a Fuji Film ultraviolet light-absorbing filter, absorbing light of a wavelength of 400 nm or shorter. The measurement of the optical density was carried out using a Macbeth Densitometer RD-514 Type (status AA filter). The change of density at the portion having an initial density of 2.0 and the change of density of the white background were measured. The results obtained are shown in Table I below.

TABLE I

| Sample | Color Image Stabilizer | Change of Yellow Density in White Background | Change of Magenta Density (Initial Density of 2.0) | Remarks |
|---|---|---|---|---|
| A | — | + 0.27 | − 1.42 | Control |
| B | Compound (3) | + 0.10 | − 0.32 | Invention |
| C | Compound (7) | + 0.11 | − 0.30 | Invention |
| D | Compound (13) | + 0.07 | − 0.28 | Invention |
| E | Compound (15) | + 0.09 | − 0.27 | Invention |
| F | Compound (17) | + 0.10 | − 0.30 | Invention |
| G | Comparative Compound (a) | + 0.25 | − 0.88 | Comparison |
| H | Comparative Compound (b) | + 0.30 | − 1.38 | Comparison |
| I | Comparative Compound (c) | + 0.23 | − 0.98 | Comparison |
| J | Comparative Compound (d) | + 0.20 | − 0.90 | Comparison |
| K | Comparative Compound (e) | + 0.25 | − 0.99 | Comparison |
| L | Comparative Compound (f) | + 0.21 | − 1.05 | Comparison |

It is apparent from the results shown in Table I above that the compounds according to the present invention are very effective for preventing light-fading of color images and also effective for preventing the yellow discoloration of the white background due to light.

Comparative Compound (a)

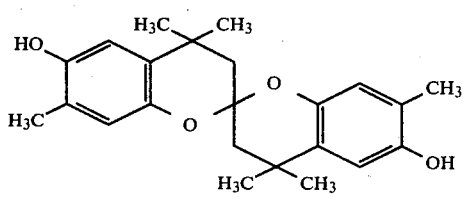

Comparative Compound (b)

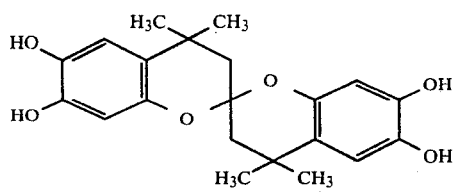

Comparative Compound (c)

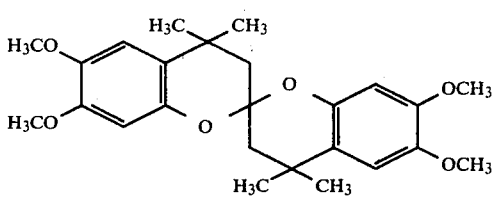

Comparative Compound (d)

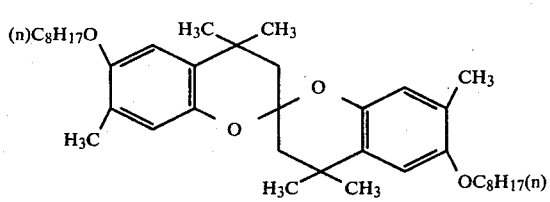

Comparative Compound (e)

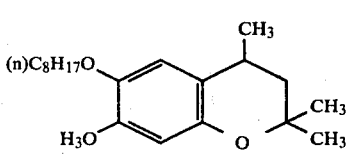

Comparative Compound (f)

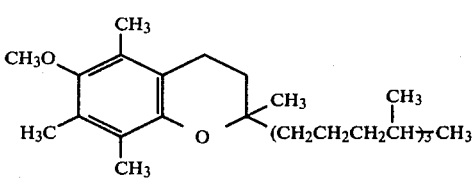

EXAMPLE 2

In the same manner as Sample A in Example 1, using the same compound as described in Example 1 as a magenta coupler, a coating composition for a third layer having the composition shown in Table III was prepared and a multilayer sample (Sample M) having the third layer shown in Table III was prepared. Also, in the same manner as Sample M described above, multilayer sample N to R each having the composition as shown in Table II were prepared. These samples were exposed and processed in the same manner as described in Example 1. Each of these samples in which dye images had been formed was subjected to a fading test for 4 weeks using a fluorescent lamp fading tester (20,000 lux). The results obtained are shown in Table II below.

TABLE II

| Sample | Color Image Stabilizer | Amount Added/10g Coupler | Change of Magenta Density (Initial Density of 1.0) | Remarks |
|---|---|---|---|---|
| M | — | — | − 0.84 | Control |
| N | Compound (15) | 3 g | − 0.18 | Invention |
| O | Compound (15) | 6 g | − 0.10 | Invention |
| P | Comparative Compound (c) | 3 g | − 0.41 | Comparison |
| Q | Comparative Compound (g) | 3 g | − 0.29 | Comparison |
| R | Compound (15) Comparative Compound (g) | 3 g<br>3 g | − 0.09 | Invention |

From the results shown in Table II above, it is apparent that the compounds according to the present invention are effective for preventing light-fading of color images and the effect remarkably increases as the increase in the amount added. Also, the effect markedly increases when the compound was used together with a known anti-fading agent such as the comparative compound (g).

Comparative Compound (g)

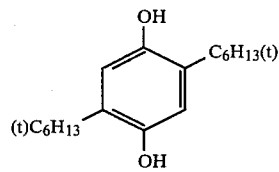

TABLE III

| | |
|---|---|
| Sixth Layer: (Protective layer) | Gelatin (1,000 mg/m$^2$) |
| Fifth Layer: (Red-sensitive layer) | Silver Chlorobromide emulsion (Br: 50 mol % . Silver: 300 mg/m$^2$), Gelatin (1,000 mg/m$^2$), Cyan coupler*$^1$ (400 mg/m$^2$), Coupler solvent*$^2$ (200 mg/m$^2$) |
| Fourth Layer: (inter layer) | Gelatin (1,200 mg/m$^2$), Ultraviolet light-absorbing agent*$^3$ (1,000 mg/m$^2$), Ultraviolet light-absorbing agent solvent*$^2$ (250 mg/m$^2$) |
| Third Layer: (Green-sensitive layer) | Silver Chlorobraomide emulsion (Br: 50 mol % . Silver: 290 mg/m$^2$), Gelatin (1,000 mg/m$^2$), Magenta Coupler*$^4$ (200 mg/m$^2$), Coupler Solvent*$^5$ (200 mg/m$^2$) |
| Second Layer: (Inter layer) | Gelatin (1,000 mg/m$^2$) |
| First Layer: (Blue-sensitive layer) | Silver Chlorobromide emulsion (Br: 80 mol % . Silver: 400 mg/m$^2$), Gelatin (1,200 mg/m$^2$), Yellow coupler*$^6$ (300 mg/m$^2$), Coupler solvent*$^7$ (150 mg/m$^2$) |
| Support: | Paper support both surfaces of which were laminated with polyethylene |

*$^1$Coupler: 2-[α-2,4-Di-tert-pentylphenoxy)-butanamido]-4,6-dichloro-5-methylphenol
*$^2$Solvent: Dibutyl phthalate
*$^3$Ultraviolet light-absorbing agent: 2-(2-Hydroxy-3-sec-butyl-5-tert-butylphenyl)-benzotriazole
*$^4$Coupler: 1-(2,4,6-Trichlorophenyl)-3-(2-chloro-5-tetradecanamido)anilino-2-pyrazolin-5-one
*$^5$Solvent: Tricresyl phosphate
*$^6$Coupler: α-Pivaloyl-α-(2,4-dioxo-5-5'-dimethyloxazolidin-3-yl)-2-chloro-5-[α-(2,4-di-tert-pentylphenoxy)butanamido]acetanilide
*$^7$Solvent: Dioctyl Butyl Phosphate While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material including a color coupler and containing, in a photographic layer thereof, at least one compound represented by the formula (I), or at least one bis-compound, including a spirobis-compounds, thereof

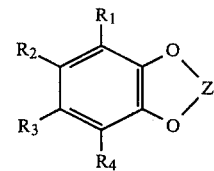

where
Z represents an alkylene group having from 1 to 3 carbon atoms or an alkylene group having from 1 to 3 carbon atoms and substituted with one or more of a halogen atom, an alkyl group, an aryl group, an alkoxy group, an aryloxy group, a =S group, or a =O group; and $R_1$, $R_2$, $R_3$ and $R_4$ each represents a hydrogen atom, a halogen atom, an alkyl group, an aryl group, an alkoxy group, an aryloxy group, an alkylthio group, an acyl group, an acylamino group, a sulfonamido group, a diacylamino group, a carboxy group, a sulfo group, or a hydroxy group, or, $R_1$ and $R_2$ or $R_2$ and $R_3$ together form a group represented by

wherein Z has the same meaning as Z in formula (I), or form a 5-membered or 6-membered carbocyclic ring or heterocyclic ring.

2. A color photographic light-sensitive material as in claim 1, wherein the substituent for Z is an alkyl group having from 1 to 32 carbon atoms, an aryl group having from 6 to 32 carbon atoms, an alkoxy group having from 1 to 32 carbon atoms, or an aryloxy having from 6 to 32 carbon atoms.

3. A color photographic light-sensitive material as in claim 2, wherein said alkyl group, aryl group, alkoxy group or aryloxy group as a substituent on Z is substituted with one or more of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

4. A color photographic light-sensitive material as in claim 1, wherein $R_1$, $R_2$, $R_3$ and $R_4$ each represents a hydrogen atom, a halogen atom, an alkyl group having from 1 to 32 carbon atoms, an aryl group having from 6 to 32 carbon atoms, an alkoxy group having from 1 to 32 carbon atoms, an aryloxy group having from 6 to 32 carbon atoms, an alkylthio group having from 1 to 32 carbon atoms, an acyl group having from 1 to 32 carbon atoms, an acylamino group having from 1 to 32 carbon atoms, a sulfonamido group having from 1 to 32 carbon atoms or a diacylamino group having from 2 to 32 carbon atoms.

5. A color photographic light-sensitive material as in claim 4, wherein said alkyl group, aryl group, alkoxy group, aryloxy group, alkylthio group, acyl group, acylamino group, sulfonamido group or diacylamino group is substituted with one or more of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

6. A color photographic light-sensitive material as in claim 1, wherein said hydrocarbon ring formed by $R_1$ and $R_2$ or $R_2$ and $R_3$, together with the benzene ring to which they are attached, is an indan ring, a spiroindan ring, a naphthalene ring or a tetrahydronaphthalene ring.

7. A color photographic light-sensitive material as in claim 1, wherein said hydrocarbon ring is substituted with one or more of a halogen atom, a nitro group, a cyano group, a thiocyano group, an alkyl group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

8. A color photographic light-sensitive material as in claim 1, wherein said compound represented by the formula (I) is represented by the formula (II).

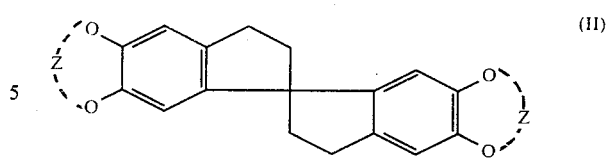

(II)

wherein Z has the same meaning as defined in claim 1.

9. A color photographic light-sensitive material as in claim 1, wherein said heterocyclic ring formed by $R_1$ and $R_2$ or $R_2$ and $R_3$, together with the benzene ring to which they are attached, is a chroman ring, a coumaran ring, a spirochroman ring, or a spirocoumaran ring.

10. A color photographic light-sensitive material as in claim 1, wherein said heterocyclic ring is substituted with one or more of a halogen atom, a nitro group, a cyano group, a thiocyano group, an alkyl group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group or a mercapto group.

11. A color photographic light-sensitive material as in claim 1, wherein said compound represented by the formula (I) is represented by the formula (III) or the formula (IV)

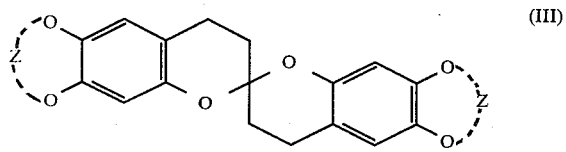

(III)

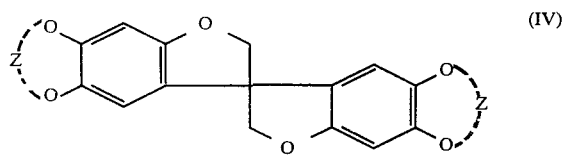

(IV)

wherein Z has the same meaning as defined in claim 1.

12. A color photographic light-sensitive material as in claim 1, wherein Z represents an unsubstituted alkylene group or an alkylene group substituted with an alkyl group or an aryl group.

13. A color photographic light-sensitive material as in claim 1, wherein $R_1$, $R_2$, $R_3$ and $R_4$ each represents a hydrogen atom, a halogen atom, an alkyl group, an alkoxy group or an alkylthio group.

14. A color photographic light-sensitive material as in claim 1, wherein $R_2$ and $R_3$ are bonded each other to form a 5-membered or 6-membered hydrocarbon ring or heterocyclic group.

15. A color photograhic light-sensitive material as in claim 1, wherein $R_2$ and $R_3$ together form a group represented by

wherein Z has the same meaning as defined in claim 1.

16. A color photographic light-sensitive material as in claim 1, wherein $R_2$ and $R_3$ together form a chroman ring or a spirochroman ring.

17. A color photographic light-sensitive material as in claim 1, wherein said compound represented by formula (I) is present in an amount of from about 0.5 to 200% by weight based on the weight of said coupler.

18. A color photographic light-sensitive material as in claim 1, wherein said compound represented by formula (I) is present in an amount of from 2 to 150% by weight based on the weight of said coupler.

19. A color photographic light-sensitive material as in claim 1, wherein said photographic layer is a light-sensitive silver halide emulsion layer.

20. A color photographic light-sensitive material as in claim 19, wherein said silver halide light-sensitive emulsion layer is a green-sensitive silver halide emulsion layer.

21. A color photographic light-sensitive material as in claim 20, wherein said green-sensitive silver halide emulsion layer contains a coupler.

22. A color photographic light-sensitive material as in claim 21, wherein said coupler is a magenta coupler.

23. A color photographic light-sensitive material as in claim 22, wherein said magenta coupler is a 5-pyrazolone type magenta coupler.

24. A color photographic light-sensitive material as in claim 19, wherein said light-sensitive silver halide emulsion layer is a red-sensitive silver halide emulsion layer.

25. A color photographic light-sensitive material as in claim 24, wherein said silver halide light-sensitive emulsion layer contains a coupler.

26. A color photographic light-sensitive material as in claim 25, wherein said coupler is a cyan coupler.

27. A color photographic light-sensitive materials in claim 26, wherein said cyan coupler is a phenol or naphthol derivative.

28. A color photographic light-sensitive material as in claim 1, wherein the compound represented by the formula (I) is used in combination with a hydroquinone compound, a hydroxychroman compound, a hydroxyspirochroman compound, a compound wherein the hydroxy group of a hydroxychroman or hydroxyspirochroman compound is substituted with an alkoxy group, or an alkoxyphenol compound.

* * * * *